(12) United States Patent
Serafin, Jr. et al.

(10) Patent No.: US 7,892,289 B2
(45) Date of Patent: Feb. 22, 2011

(54) IMPLANT BORE INSERT

(75) Inventors: Louis A. Serafin, Jr., Lakeport, MI (US); Nicholas H. Burlingame, Belmont, NY (US)

(73) Assignee: Signal Medical Corporation, Marysville, MI (US)

( * ) Notice: Subject to any disclaimer, the term of this patent is extended or adjusted under 35 U.S.C. 154(b) by 1274 days.

(21) Appl. No.: 11/391,823

(22) Filed: Mar. 29, 2006

(65) Prior Publication Data

US 2006/0188845 A1    Aug. 24, 2006

Related U.S. Application Data

(63) Continuation-in-part of application No. PCT/US2004/032041, filed on Sep. 30, 2004.

(60) Provisional application No. 60/507,872, filed on Oct. 1, 2003, provisional application No. 60/677,241, filed on May 3, 2005.

(51) Int. Cl.
*A61F 2/36* (2006.01)
*A61C 5/08* (2006.01)

(52) U.S. Cl. .................................. 623/22.45; 433/172

(58) Field of Classification Search ............... 623/19.12, 623/20.22, 21.17, 22.4, 22.42, 22.43, 22.44, 623/22.45, 22.46, 23.11, 23.12, 23.13, 23.4; 433/172, 173, 201.1, 204, 220
See application file for complete search history.

(56) References Cited

U.S. PATENT DOCUMENTS

| | | | |
|---|---|---|---|
| 4,032,994 A | | 7/1977 | Frey |
| 4,253,835 A | * | 3/1981 | Ware ........................... 433/220 |
| 4,687,488 A | * | 8/1987 | Frey ......................... 623/22.45 |
| 4,842,605 A | | 6/1989 | Sonnerat et al. |
| 4,921,500 A | | 5/1990 | Averill et al. |
| 5,015,257 A | * | 5/1991 | Crowninshield et al. . 623/22.45 |
| 5,080,679 A | * | 1/1992 | Pratt et al. ................ 623/23.38 |
| 5,152,795 A | * | 10/1992 | Sioshansi et al. ............ 424/423 |
| 5,362,311 A | | 11/1994 | Amino et al. |
| 6,290,500 B1 | * | 9/2001 | Morgan et al. .............. 433/173 |
| 2004/0063069 A1 | * | 4/2004 | Lombardi .................... 433/173 |

OTHER PUBLICATIONS

CeramTec AG, BIOLOX (Reg. U.S. Pat. & Tm. Off.) option Ball Head System brochure. Date appears to be Oct. 2004.

* cited by examiner

*Primary Examiner*—Eduardo C Robert
*Assistant Examiner*—David Comstock
(74) *Attorney, Agent, or Firm*—Christopher John Rudy

(57) ABSTRACT

Implant bore insert has an outer surface that is, at least in part, substantially cylindrically aligned. The insert may be blind, thus forming a cup, or it may be open ended. The insert can be provided with a predetermined outer circumferential surface that provides for a suitable interference fit with a corresponding bore hole of an implant component part. When inserted into the bore hole, the insert preferably seats itself on a blind end of the bore hole. Examples of implants employed with the insert can include ceramic ball joint heads and teeth.

20 Claims, 3 Drawing Sheets

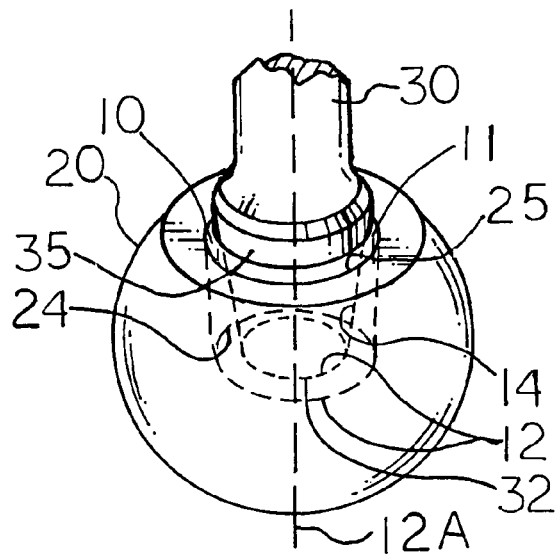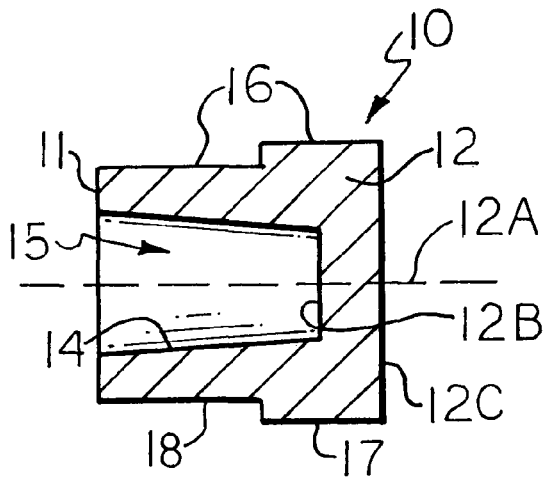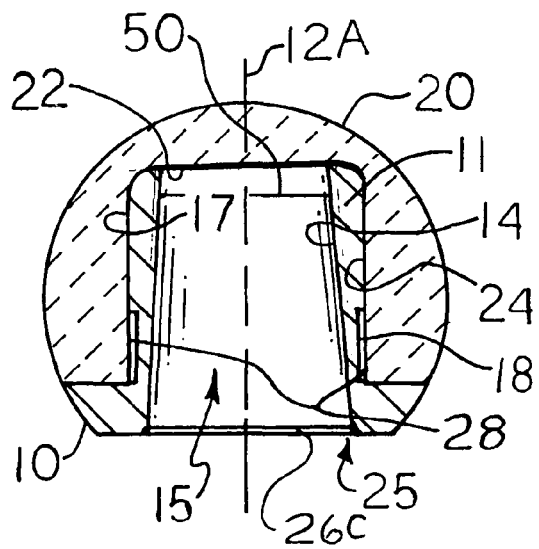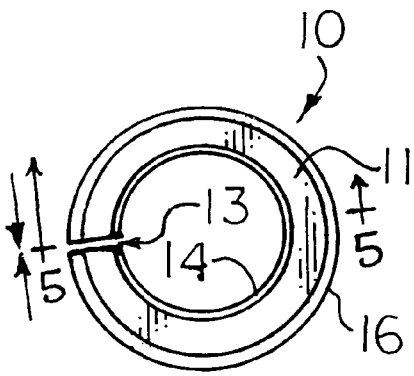

IMPLANT BORE INSERT

This is a continuation-in-part of international patent application No. PCT/US2004/032041 filed on Sep. 30, 2004 A.D., and claims domestic priority benefits of U.S. Provisional Patent Application Nos. 60/507,872 filed on Oct. 1, 2003 A.D., and 60/677,241 filed on May 3, 2005 A.D., the same being claimed pursuant to 35 USC 119(e); 120; 363 and/or 365, and so forth. The specifications of those three applications are incorporated herein by reference in their entireties.

BACKGROUND TO THE INVENTION

I. Field

The present invention concerns an insert for an implant bore, and the implant with the bore insert. For example, a ceramic hip joint ball or a ceramic tooth bore can have a metal bore insert.

II. Art

Various orthopedic and dental implant devices are known.

Ceramic ball joints for the hip, for example, may contain a tapered bore hole into which a suitably tapered metal stem is inserted. A problem with this is that, should there be a slight mismatch of the trunnion of the stem with the ceramic bore, or a defect such as a burr on the trunnion, the implant may fail, even at its assembly. In attempting to address this problem, Amino et al., U.S. Pat. No. 5,362,311, disclosed an artificial hip joint in which a tapered cone of a metallic stem is inserted into a tapered hole of a ceramic head, with a truncated conical sleeve compressingly held in the tapered hole of the head. Compare, Averill et al., U.S. Pat. No. 4,921,500; Sonnerat et al., U.S. Pat. No. 4,842,605; and Frey, U.S. Pat. No. 4,032,994. See also, BIOLOX (Reg. U.S. Pat. & Tm. Off.) option Ball Head System, CeramTec AG.

Also, certain dental implants are made of ceramic and have a bore into which a stem is inserted. The stem may be affixed to the patient's jaw and so forth.

It would be desirable to improve upon the art.

DISCLOSURE OF THE INVENTION

It has been found that a problem with the device of the '311 patent is that, although there may be hoop stress in the ceramic ball, it may significantly change with stem insertion. Also, the sleeve does not contact the blind end of the ball's tapered hole, and compressive load stress on the ball from the stem is absent.

Such stress characteristics may lead to implant failure.

Accordingly, it is an object to ameliorate the foregoing.

It is an object of the invention to improve upon and/or provide alternative implant devices to the art.

It is another object of the present invention to provide a novel joint implant bore insert, and an implant with the insert.

It is another object hereof to provide a novel hip joint implant ball insert, and a hip ball and a femoral component with the hip ball, which have the insert.

It is a further object hereof to provide a novel tooth implant bore insert, and a tooth with the insert.

At least one of these or other objects are satisfied, if not wholly, at least in part, by an implant bore insert that has an outer surface that is, at least in part, substantially cylindrically aligned. The insert may be blind, thus forming a cup, or it may be open ended. Preferably, the insert is provided with a predetermined outer circumferential surface that provides for a suitable interference fit with a corresponding bore hole of an implant component part. When inserted into the bore hole, the insert preferably seats itself on a blind end of the bore hole. The insert can also seat on a step located before the blind end of the bore hole.

Significantly, by the invention, especially in its preferred embodiments, a stress-bearing ceramic implant component part having a bore hole into which a stem or other part is inserted can be generally protected from problems associated with the insertion of slightly mismatched or misaligned metal stems and so forth. As examples, ceramic hip balls and teeth can be provided with such an insert. Natural teeth can be augmented internally, for instance, by cement, ceramic and/or metal, if desired or necessary, and provided such a hole and insert to receive analogous treatment and be implanted in accordance with the practice of the present invention. A particularly notable benefit is the control of hoop stress and other radial stress that may be undesirable, and the provision of the compressive load stress through the blind end of the bore hole of the part.

Numerous further advantages attend the invention.

The drawings form part of the specification hereof. With respect to the drawings, which are not necessarily drawn to scale, the following is briefly noted:

FIG. 1 is a perspective plan view of an implant bore insert of the invention, inserted into a bore of a component part, and into which a stem is inserted, the same embodied as a ceramic ball hip joint implant with a metal cup insert and a metal stem.

FIG. 2 is a side sectional view of the insert in FIG. 1.

FIG. 3 is a side sectional plan view of another implant bore insert of the invention, inserted into the bore of a component part, embodied as a ceramic ball hip joint implant with an open-ended metal insert.

FIG. 4 is a top plan view of another implant bore insert of the invention embodied for a hip.

Figure 5:
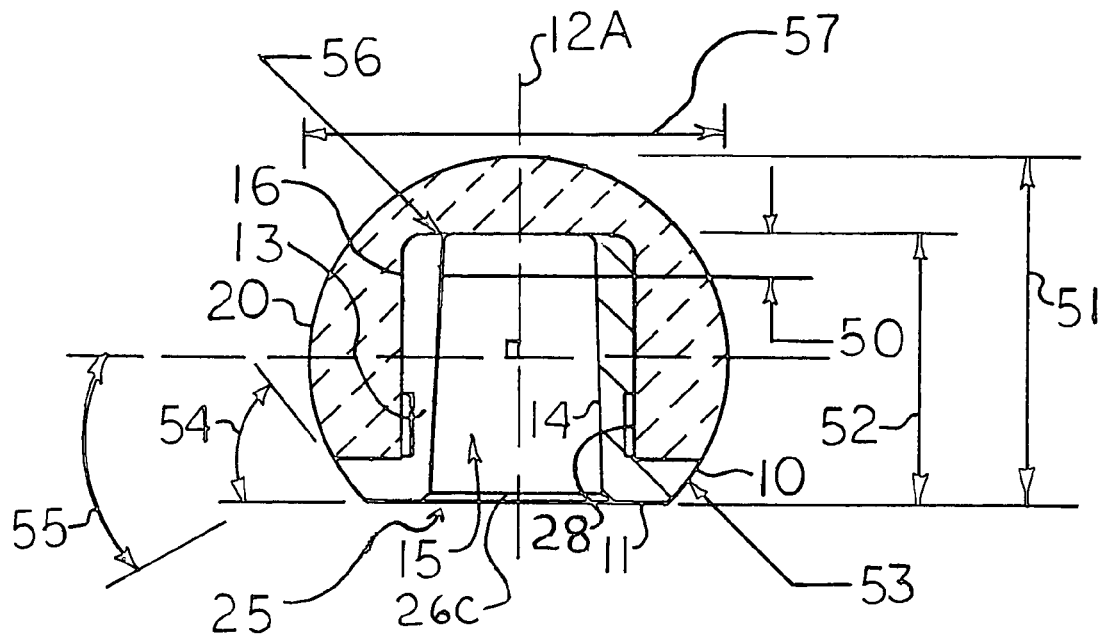
FIG. 5 is a side sectional plan view of the insert depicted in FIG. 4, taken along 5-5 of FIG. 4, inserted into the bore of a ceramic ball.

The invention can be further understood by the detail set out below, which may be read in view of the drawings. Such is to be taken in an illustrative and not necessarily limiting sense.

The insert of the invention can be employed with virtually any suitable component part having a corresponding bore hole for insertion of a stem or other component part. Accordingly, the corresponding bore hole can have, at least in part, a substantially cylindrical side wall. Thus included among implants with which the insert may be employed are load-bearing joint implants to include enarthrodial joint balls such as, for example, for the hip, which may be a conventional, smaller ball for total hip replacement or a larger ball for hemi or total hip replacement, sometimes referred to as a "resurfacing" hip, the shoulder, a digit, and so forth; ginglymous joint components such as those of the knee, elbow, or ankle. Beneficially, the implant component is for an articulating joint such as the hip, shoulder, digit, knee, elbow, ankle, and so on. Thus, for example, various femoral hip and humeral shoulder components can be improved, as well as can metacarpal or phalangeal finger and thumb components, femoral and tibial knee components, and so forth and the like. A highly advantageous embodiment for the insert of the invention is a tooth. Such implant components are advantageously for humans.

The implant component into which will be inserted the insert can be made of any suitable material. Preferably, the material is a suitable ceramic, which, in general, may include a boride, oxide, carbide, nitride and/or silicate, say, of Al, Si, Sc, Y, La, a lanthanide series element, Ac, an actinide series element, Ti, Zr, Hf, V, Nb and/or Ta, and so forth and the like. However, the ceramic is especially a zirconia ceramic, and most especially a magnesium oxide stabilized zirconia ceramic. Such a ceramic may be made from a micropowder, or from a nanopowder where the powder precursors are less that about two hundred nanometers and the formed grain structure reflects this nanotechnology.

The insert may be made of any suitable material. A preferred material for the insert is a biocompatible metal or alloy. For instance, the biocompatible metal or alloy may be a cobalt metal alloy such as one conforming to ASTM-F-75, preferably ASTM-F-799 or ASTM-F-1537, or a titanium metal alloy such one conforming to ASTM-F-67, preferably ASTM-F-136 or ASTM-F-1472.

The insert, although it has a body with an outer surface that is, at least in part, substantially cylindrically aligned, may take any of numerous forms. It has an inner surface that can receive a stem or other component part, and this inner surface can be tapered, cylindrical, ovoid, polygonal, threaded, and so forth. Preferably, the inner surface is tapered conically or especially truncated conically, for example, with a Morse or Browne and Sharpe taper, to receive the corresponding stem or other part, which itself is preferably of biocompatible metal.

With respect to the drawings, metal insert 10 includes side wall 11 and may include roof 12 orthogonal to standard long axis 12A, with blind end 12B and cup end 12C. The insert 10 may complete a circumferential circuit (FIGS. 1-3, 6, 7) or have gap 13 (FIGS. 4,5). Inner surface 14 has Morse taper. Receiving hole 15 can receive stem 30. Outer surface 16 is at least in part a cylinder, and has outer circumference providing for a suitable interference fit with a corresponding bore hole of an implant component part. The outer surface 16 may be subdivided into proximal section 17 and distal section 18, with the proximal section 17 having the predetermined outer circumferential surface that provides for the interference fit, for example, as can be provided by scratched surface 19 for a 0.001-inch interference fit with a corresponding machined bore hole. The proximal section 17 may be threaded, grooved or otherwise roughened to aid insertion and/or gripping. Implant component part 20 is depicted as a ceramic hip ball (FIGS. 1-6) or ceramic tooth (FIG. 7), each of which has end 22 orthogonal to cylindrical wall 24, which define bore hole 25, which can be considered to have opening portion 28. When inserted into the bore hole 25, the insert 10 seats on the blind end 22 of the bore hole 25 (FIGS. 1, 3, 5, 7), to include with the cup end 12 C (FIGS. 1, 7). Advantageously, the distal section 18 does not contact the opening portion 28 of the bore hole 25, preferably for a distance of about from ten to fifty percent of the overall depth of the bore hole 25, i.e., about from ten to fifty percent of the distance along the wall 24 from the outer opening to the end 22 of the bore hole 25 (FIGS. 3, 5, 7) which can improve stress related characteristics of the system. The insert 10 can extend beyond the opening of the bore hole 25, which can allow extended neck or stem 30 lengths, preferably up to the depth of the bore hole 25, and can allow outer shelf or shoulder 26 that is larger than the diameter of the bore hole 25 to allow the insert 10 to rest on a truncation adjacent the bore hole opening 28, and chamfer 26C may be provided about the opening of the bore hole 15 (FIGS. 3, 5, 7).

The insert 10 may be shrunk fit, for example, by cooling it before insertion into the part 20 and allowing it to warm up to ambient temperature thus causing expansion of the insert 10 to press against the wall 24 of the bore 25, or it may be secured by active metal brazing, as known in the art. Larger diameter proximal section 17 with smaller diameter distal section 18 generally limits stress more central to the part 20 as a ball and avoids stress about the opening 28 of the bore 25.

The metal stem 30 may have proximal end 32 on trunnion 35 with Morse taper, which fits into the receiving hole 15 of the insert 10. When inserted into the receiving hole 15, the end 32 of the trunnion 35 may seat on the blind end 12B of the insert 10 (FIGS. 1, 7) or seats on end 22 of the bore hole 25 (FIGS. 3, 5).

Dimensions can be any which are suitable. In further reference to the drawings, examples of dimensions, which may be considered to be approximate or precise, and further features can include those set forth in the tables which follow.

TABLE 1

Some comments and dimensions for FIGS. 3 and 5

| FIG.(s) | Number | Comment/Dimension |
|---|---|---|
| 3, 5 | 50 | Gage height, 2.70 mm (FIG. 5) |
| 5 | 51 | Overall height, 25.5 mm ± 0.15 mm |
|  | 52 | Insert height, 20.0 mm ± 0.15 mm |
|  | 53 | Laser mark (indicia) on chamfer, centered, letter height 1~2 mm |
|  | 54 | First angle, 50 ± 2 degrees |
|  | 55 | Second angle, 30 ± 2 degrees |
|  | 56 | Radius, 0.5 mm |
|  | 57 | Diameter, 28.00 mm + 0.00 mm − 0.05 mm; sphere, 0.005 mm; radius, 0.02 um |

TABLE 2

Figure 6:
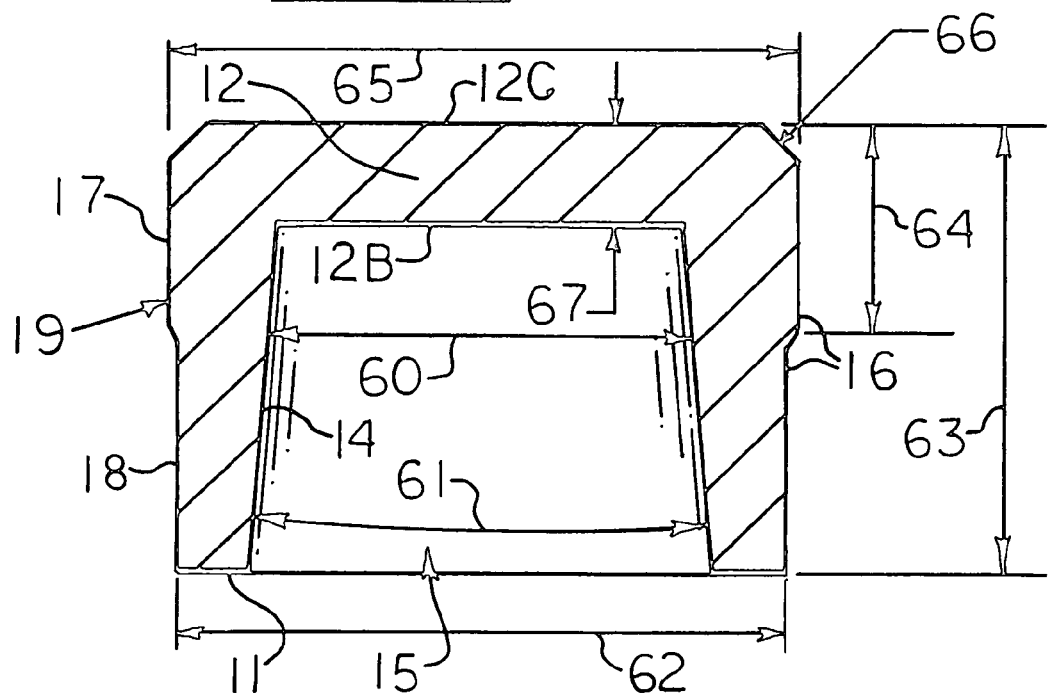
FIG. 6 is a side sectional view of another implant bore insert of the invention, embodied as a ceramic ball hip joint implant metal cup insert, say, for a 28-mm conventional implant.
Figure 7:
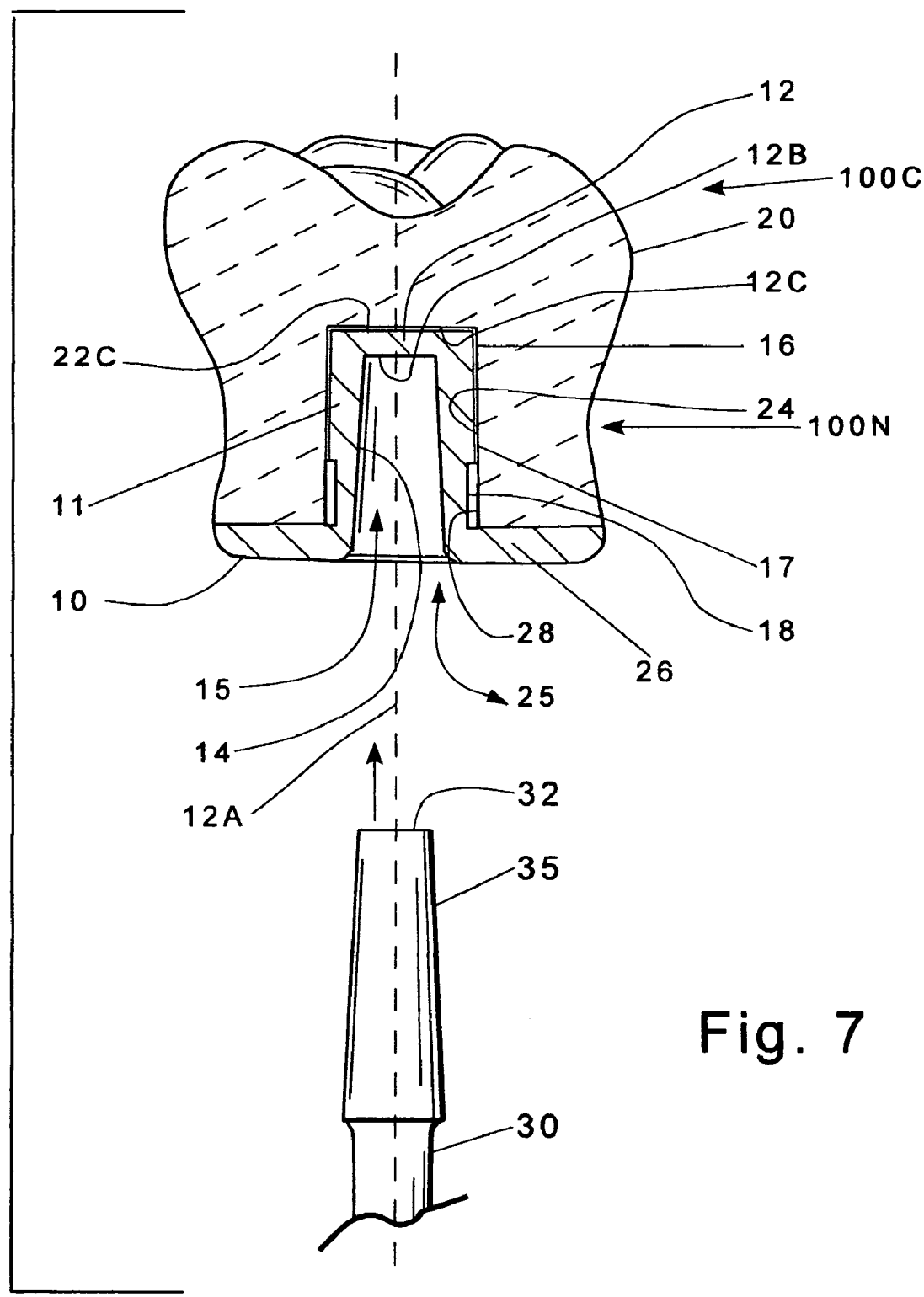
FIG. 7 is a side, cross sectional, exploded view of another implant bore insert of the invention, embodied as a tooth bore insert, inserted into a bore in a ceramic tooth component part, and into which a stem can be inserted, the same embodied as a molar with a metal cup insert and a metal stem.

Some comments and dimensions for FIG. 6
for insert made, for insert made, for example, of Ti 6-4
(ASTM F-136 or ASTM F-1472)

| Number | Comment/Dimension |
|---|---|
| 60 | Gage height, where trunnion engages, diameter 0.5005 inches ± 0.0010 inches (1.271 cm ± 0.0025 cm) |
| 61 | Taper, 5.72 + 0.07 − 0.04 degrees |
| 62 | Outside distal rim diameter, 0.677 inches (1.72 cm) |
| 63 | Basic height, 0.500 inches (1.27 cm) |
| 64 | Proximal height, 0.265 inches (0.673 cm) |
| 65 | Outside proximal section diameter, 0.6880 ± 0.0001 inches (1.748 ± 0.0003 cm), say, for 0.686-inch (1.74-cm) bore |
| 66 | Chamfer or radius, e.g., 0.020-inch (0.051-cm) radius |
| 67 | End thickness, 0.120 inch (0.305 cm) |

Again, the implant component as depicted, into which may be inserted the insert 10, can be embodied as a hip ball (FIGS. 1, 3 and 5) or a tooth (FIG. 7). The tooth may include crown 100C and neck 100N.

The present invention is thus provided. Various feature(s), subcombination(s) and/or combination(s) can be employed with or without reference to other feature(s), part(s), (s) and/or combination(s) in the practice of the invention, and numerous adaptations and modifications can be in its spirit, the literal claim scope of which is pointed out as follows:

What is claimed is:

1. An implant bore insert comprising a body of one and only one piece that has a side wall, which has:
   an inner surface that can receive a first component part of an implant, wherein the inner surface is tapered with one and only one taper angle to receive the first component part of the insert, which has a corresponding outer taper; and
   an outer surface that can be inserted into a bore hole in a second component part of the implant and that is, at least in substantial part, substantially cylindrical with, excluding any rounded proximal end, substantially one and only one radius at or near the proximal end of the insert that is first inserted into the implant bore so as to lack a proximal step feature, wherein the outer surface has a distal section, at least a portion of which is less in dimension than that of a proximal section of the outer surface, at least the proximal section being for insertion into the bore hole.

2. The insert of claim 1, which is blind and forms a cup.

3. The insert of claim 1, which is open ended.

4. The insert of claim 1, which is made of a biocompatible metal or metal alloy.

5. The insert of claim 1, wherein the outer surface has the rounded proximal end.

6. The insert of claim 1, wherein the insert is blind and forms a cup.

7. The insert of claim 1, which has a shoulder that extends outwardly from a distal section of the outer surface.

8. An implant component comprising, in combination:
   an implant bore insert having a body of one and only one piece that has a side wall, which has an inner surface that can receive a first component part of an implant, wherein the inner surface is tapered with one and only one taper angle to receive the first component part of the insert, and which has an outer surface that can be inserted into a bore hole in a second component part of the implant and that is, at least in substantial part, substantially cylindrical, with, excluding any rounded proximal end, substantially one and only one radius at or near the proximal end of the insert that is first inserted into the implant bore so as to lack a proximal step feature, wherein the outer surface of the insert has a distal section, at least a portion of which is less in dimension than that of a proximal section of the outer surface of the insert, at least the proximal section of the outer surface of the insert being inserted into and received by the bore hole; and
   the second implant component part, into the bore hole of which the insert is inserted, the bore hole having, at least in substantial part, a substantially cylindrical side wall.

9. The combination of claim 8, wherein the outer surface of the insert is provided with a predetermined outer circumferential surface, which is substantially cylindrical and which provides for an interference fit with the bore hole of the second implant component part.

10. The combination of claim 9, wherein the second implant component part having the bore hole is ceramic, and the insert seats itself on a blind end of the bore hole.

11. The combination of claim 8, wherein the first implant component part embraces a stem, and the combination also has the stem inserted and received in the implant bore insert.

12. The combination of claim 8, wherein the second implant component part having the bore hole is a ceramic ball for a hip joint implant.

13. The combination of claim 8, wherein the second implant component part having the bore hole is a tooth implant.

14. The combination of claim 8, wherein the outer surface of the insert is rounded at its proximal end.

15. The combination of claim 14, wherein the first implant component part embraces a stem, which is present and received into the insert and which has a trunnion with an outer surface that is correspondingly tapered to the inner surface of the insert.

16. The combination of claim 8, wherein the insert has a shoulder that extends outwardly from a distal section of the outer surface beyond an opening of the bore hole of the second implant component part having the bore hole.

17. The combination of claim 16, wherein the shoulder of the insert rests on an outer truncated surface of the second implant component part having the bore hole.

18. The combination of claim 8, wherein the insert is shrunk fit into the second implant component part having the bore hole.

19. An implant component for a stress-bearing implant, which comprises:
   an implant bore insert embracing a body of one and only one piece that has a side wall, which has an inner surface that can receive a first component part of an implant, wherein the inner surface is tapered with one and only one taper angle to receive the first component part of the insert, and which has an outer surface that can be inserted into a bore hole in a second component part of the implant and that is, at least in substantial part, substantially cylindrical, with, excluding any rounded proximal end, substantially one and only one radius at or near the proximal end of the insert that is first inserted into the implant bore so as to lack a proximal step feature, wherein the implant bore insert is of a biocompatible metal or metal alloy; and
   the second implant component part, into the bore hole of which the insert is inserted, the bore hole having, a blind end, and, at least in substantial part, a substantially cylindrical side wall, wherein the second implant component part is of ceramic;
wherein hoop stress and other radial stress is controlled, and compressive load stress through the blind end of the bore hole is provided.

20. The implant component of claim 19, wherein the ceramic of the second implant component part is a magnesium oxide stabilized zirconia.

* * * * *